(12) United States Patent
Fassih et al.

(10) Patent No.: US 8,150,525 B2
(45) Date of Patent: Apr. 3, 2012

(54) TREATMENT OF HYPERHYDROSIS (75) Inventors: Ali Fassih, Franklin Park, NJ (US); Ronald J. Gillespie, North Brunswick, NJ (US); Michael Joyce, Randolph, NJ (US); Joseph Junio, Edison, NJ (US); Joan D. Newburger, West Trenton, NJ (US); Ying Sun, Belle Mead, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 763 days.

(21) Appl. No.: 12/199,018

(22) Filed: Aug. 27, 2008

(65) Prior Publication Data

US 2010/0057147 A1 Mar. 4, 2010

(51) Int. Cl.
*A61N 1/18* (2006.01)

(52) U.S. Cl. ........... 607/50; 607/111; 607/144; 607/149

(58) Field of Classification Search ............... 607/50, 607/111, 144, 149
See application file for complete search history.

(56) References Cited

U.S. PATENT DOCUMENTS

| | | |
|---|---|---|
| 4,067,342 A | 1/1978 | Burton |
| 4,211,222 A | 7/1980 | Tapper |
| 4,305,390 A | 12/1981 | Swartz |
| 4,372,296 A | 2/1983 | Fahim |
| 4,406,658 A | 9/1983 | Lattin et al. |
| 4,474,570 A | 10/1984 | Ariura et al. |
| 4,606,354 A | 8/1986 | Jacob |
| 4,767,401 A | 8/1988 | Seiderman |
| 4,842,577 A | 6/1989 | Konno et al. |
| 4,852,571 A | 8/1989 | Gadsby et al. |
| 4,956,184 A | 9/1990 | Kross |
| 4,957,480 A | 9/1990 | Morenings |
| 4,979,938 A | 12/1990 | Stephen et al. |
| 5,042,975 A | 8/1991 | Chien et al. |
| 5,147,297 A | 9/1992 | Myers et al. |
| 5,162,043 A | 11/1992 | Lew et al. |
| 5,224,927 A | 7/1993 | Tapper |
| 5,298,017 A | 3/1994 | Theeuwes et al. |
| 5,314,502 A | 5/1994 | McNichols et al. |
| 5,326,341 A | 7/1994 | Lew et al. |
| 5,338,412 A | 8/1994 | Burk et al. |
| 5,352,315 A | 10/1994 | Carrier et al. |

(Continued)

FOREIGN PATENT DOCUMENTS

EP 0 337 642 A 10/1989

(Continued)

OTHER PUBLICATIONS

Data sheet ionto Patch publicly available prior to Jun. 30, 2003.

(Continued)

*Primary Examiner* — Scott Getzow
*Assistant Examiner* — Joseph Dietrich (57) ABSTRACT

A device for the treatment of hyperhydrosis by application of electric current to a treatment area of the skin is described. The device comprises: a) a garment comprising a first electrode adapted for contacting said treatment area; b) a second electrode adapted for contacting the treatment area or skin proximal to the treatment area; and c) a power delivery unit in electrical communication with said first and second electrodes. The power delivery unit provides a customized dose of electricity to the treatment area. In one embodiment, the garment is a glove.

27 Claims, 5 Drawing Sheets

U.S. PATENT DOCUMENTS

| | | |
|---|---|---|
| 5,356,632 A | 10/1994 | Gross et al. |
| 5,380,272 A | 1/1995 | Gross |
| 5,384,134 A | 1/1995 | Kross et al. |
| 5,387,189 A | 2/1995 | Gory et al. |
| 5,405,317 A | 4/1995 | Myers et al. |
| 5,415,628 A | 5/1995 | Untereker et al. |
| 5,428,185 A | 6/1995 | Kunimoto et al. |
| 5,443,441 A | 8/1995 | De Claviere |
| 5,466,217 A | 11/1995 | Myers et al. |
| 5,470,349 A | 11/1995 | Kleditsch et al. |
| 5,624,415 A | 4/1997 | Ledger et al. |
| 5,624,425 A | 4/1997 | Gray et al. |
| 5,637,084 A | 6/1997 | Kontturi et al. |
| 5,678,545 A | 10/1997 | Stratbucker |
| 5,685,837 A | 11/1997 | Horstmann |
| 5,688,233 A | 11/1997 | Hofmann et al. |
| 5,817,044 A | 10/1998 | Evers et al. |
| 5,855,570 A | 1/1999 | Scherson et al. |
| 5,897,522 A | 4/1999 | Nitzan |
| 5,928,185 A | 7/1999 | Muller et al. |
| 5,935,598 A | 8/1999 | Sage et al. |
| 5,955,017 A | 9/1999 | Fofano et al. |
| 5,955,067 A | 9/1999 | Oge et al. |
| 5,961,483 A | 10/1999 | Sage et al. |
| 5,974,344 A | 10/1999 | Shoemaker, II |
| 5,985,308 A | 11/1999 | Burrell et al. |
| 5,993,435 A | 11/1999 | Haak et al. |
| 6,004,309 A | 12/1999 | Phipps |
| 6,038,485 A | 3/2000 | Axelgaard |
| 6,078,842 A | 6/2000 | Gross et al. |
| 6,104,950 A | 8/2000 | Higo et al. |
| 6,113,636 A | 9/2000 | Ogle |
| 6,157,858 A | 12/2000 | Gross et al. |
| 6,169,920 B1 | 1/2001 | Haak et al. |
| 6,185,453 B1 | 2/2001 | Hussain et al. |
| 6,223,076 B1 | 4/2001 | Tapper |
| 6,231,830 B1 | 5/2001 | Madray |
| 6,238,381 B1 | 5/2001 | Tapper |
| 6,248,449 B1 | 6/2001 | Watanabe |
| RE37,263 E | 7/2001 | Kross et al. |
| 6,275,372 B1 | 8/2001 | Vassallo et al. |
| 6,289,241 B1 | 9/2001 | Phipps |
| 6,302,874 B1 | 10/2001 | Zhang et al. |
| 6,306,384 B1 | 10/2001 | Lahanas et al. |
| 6,317,629 B1 | 11/2001 | Haak et al. |
| 6,385,487 B1 | 5/2002 | Henley |
| 6,421,561 B1 | 7/2002 | Morris |
| 6,424,862 B1 | 7/2002 | Brown, III et al. |
| 6,443,978 B1 | 9/2002 | Zharov |
| 6,455,065 B1 | 9/2002 | Hymes |
| 6,488,965 B1 | 12/2002 | Karageozian |
| 6,494,900 B1 | 12/2002 | Salansky et al. |
| 6,495,158 B1 | 12/2002 | Buseman et al. |
| 6,522,918 B1 | 2/2003 | Crisp et al. |
| 6,544,401 B1 | 4/2003 | Colic |
| 6,552,895 B1 | 4/2003 | Vassallo et al. |
| 6,560,483 B1 | 5/2003 | Kumar et al. |
| 6,582,416 B2 | 6/2003 | Tapper |
| 6,584,349 B1 | 6/2003 | Sage, Jr. et al. |
| 6,631,294 B2 | 10/2003 | Andino et al. |
| 6,653,014 B2 | 11/2003 | Andreson et al. |
| 6,654,635 B1 | 11/2003 | Koga et al. |
| 6,708,050 B2 | 3/2004 | Carim |
| 6,735,470 B2 | 5/2004 | Henley et al. |
| 6,738,662 B1 | 5/2004 | Frank |
| 6,745,071 B1 | 6/2004 | Anderson et al. |
| 6,766,202 B2 | 7/2004 | Underwood et al. |
| 6,775,570 B2 | 8/2004 | Joshi |
| 6,821,281 B2 | 11/2004 | Sherman et al. |
| 6,855,117 B2 | 2/2005 | Skover |
| 6,866,856 B2 | 3/2005 | Lu et al. |
| 6,890,553 B1 | 5/2005 | Sun et al. |
| 6,989,156 B2 | 1/2006 | Gillis |
| 7,005,408 B2 | 2/2006 | Ahmad et al. |
| 7,008,647 B2 | 3/2006 | Burrell et al. |
| 7,457,667 B2 | 11/2008 | Skiba |
| 7,476,221 B2 | 1/2009 | Sun et al. |
| 7,476,222 B2 | 1/2009 | Sun et al. |
| 7,477,938 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,480,530 B2 | 1/2009 | Sun et al. |
| 7,486,989 B2 | 2/2009 | Sun et al. |
| 7,495,146 B2 | 2/2009 | Crisp |
| 7,507,228 B2 | 3/2009 | Sun et al. |
| 2002/0099320 A1 | 7/2002 | Beck |
| 2002/0173743 A1 | 11/2002 | Tapper |
| 2002/0173833 A1 | 11/2002 | Koman et al. |
| 2002/0183685 A1 | 12/2002 | Crawford et al. |
| 2002/0188241 A1 | 12/2002 | Morris et al. |
| 2003/0023270 A1 | 1/2003 | Danz et al. |
| 2003/0028170 A1 | 2/2003 | Anderson et al. |
| 2003/0039860 A1 | 2/2003 | Cheon et al. |
| 2003/0054046 A1 | 3/2003 | Burrell |
| 2003/0059673 A1 | 3/2003 | Langan et al. |
| 2003/0149393 A1 | 8/2003 | Joshi |
| 2003/0176832 A1 | 9/2003 | Rossi |
| 2003/0216783 A1 | 11/2003 | Lehtoluoto |
| 2004/0006374 A1 | 1/2004 | Mondin |
| 2004/0043062 A1 | 3/2004 | Sun |
| 2004/0044384 A1* | 3/2004 | Leber et al. ............ 607/96 |
| 2004/0167460 A1 | 8/2004 | Anderson et al. |
| 2004/0167461 A1 | 8/2004 | Nitzan et al. |
| 2004/0265395 A1 | 12/2004 | Sun et al. |
| 2004/0267189 A1 | 12/2004 | Mavor |
| 2004/0267190 A1 | 12/2004 | Tamarkin et al. |
| 2004/0267236 A1 | 12/2004 | Sun et al. |
| 2004/0267237 A1 | 12/2004 | Sun et al. |
| 2005/0004509 A1 | 1/2005 | Sun et al. |
| 2005/0010192 A1 | 1/2005 | Sun et al. |
| 2005/0148996 A1 | 7/2005 | Sun et al. |
| 2006/0015052 A1 | 1/2006 | Crisp |
| 2006/0015053 A1 | 1/2006 | Crisp |
| 2007/0003516 A1 | 1/2007 | Almond et al. |
| 2007/0060862 A1 | 3/2007 | Sun et al. |
| 2007/0122461 A1 | 5/2007 | Ko |
| 2007/0141173 A1 | 6/2007 | Miyamoto et al. |
| 2007/0191756 A1 | 8/2007 | Tapper |
| 2008/0050452 A1 | 2/2008 | Chen et al. |
| 2009/0123733 A1 | 5/2009 | Ohrlander et al. |
| 2009/0292328 A1* | 11/2009 | Birkill et al. ............ 607/149 |

FOREIGN PATENT DOCUMENTS

| | | |
|---|---|---|
| EP | 0 532 451 A | 3/1993 |
| EP | 1 008 365 A | 6/2000 |
| EP | 1 484 012 A | 12/2004 |
| GB | 2206493 A | 1/1989 |
| JP | 03 080874 A | 4/1991 |
| JP | 10 024108 A | 1/1998 |
| WO | WO 89/01764 A1 | 3/1989 |
| WO | WO 93/00959 A | 1/1993 |
| WO | WO 93/14813 A1 | 8/1993 |
| WO | WO 94/11058 A | 5/1994 |
| WO | WO 94/16765 A1 | 8/1994 |
| WO | WO 94/17853 A1 | 8/1994 |
| WO | WO 97/06847 A | 2/1997 |
| WO | WO 98/14237 A | 4/1998 |
| WO | WO 99/43382 A | 2/1999 |
| WO | WO 99/56819 A | 11/1999 |
| WO | WO 00/12173 A | 3/2000 |
| WO | WO 00/47274 A1 | 8/2000 |
| WO | WO 00/62856 A1 | 10/2000 |
| WO | WO 00/62857 A1 | 10/2000 |
| WO | WO 00/74772 A | 12/2000 |
| WO | WO 01/80945 A | 11/2001 |
| WO | WO 02/098502 A | 12/2002 |
| WO | WO 03/082095 A | 10/2003 |
| WO | WO 2005/004979 A1 | 1/2005 |
| WO | WO 2005/004981 A2 | 1/2005 |
| WO | WO 2005/004982 A2 | 1/2005 |
| WO | WO 2005/004983 A2 | 1/2005 |
| WO | WO 2005/004984 A | 1/2005 |
| WO | WO 2006/133134 A2 | 12/2006 |
| WO | WO 2008/079898 A1 | 7/2008 |
| WO | WO 2009/045720 A2 | 4/2009 |

OTHER PUBLICATIONS

Electrochemistry Handbook Table 14.1, McGraw Hill Inc. 1995 pp. 14-3-14.16.

Davis, Can Acupuncture Punch Up Your Appearance?, Wall Street Journal Health Article, Dec. 21, 2004, p. 107.

Li et al., Ultra Zinc and Nickel, Palladium, Silver Coated Zinc Particles Used for Reductive Dehalogenation of chlorinated Ethylenes in Aqueous Solution, Croatica chemical Acta CCACAA 71 (4) 853-872 (1998).

Sato et al., Generation and transit pathway of H+ is critical for inhibition of palmar sweating by iontophoresis in water, J. Applied Physiology, Nov. 1993; 75: 2258-2264.

Spacciapoli et al., Antimicrobial ativity of silver nitrate against periodoental pathogens, Journal of Peridontal Research, 2001, 36:108-113.

Stux et al., Basics of Acupuncture, Springer 2003 pp. 306-309.

Procellera™ bioelectric wound dressing, Vomaris Wound Care, Inc., distributed Oct. 22-25, 2009 at 2009 Clinical Symposium on Advances in Skin and Wound Care, San Antonio, TX.

Ly Chan et al., Treatment of palmar hyperhidrosis using tap water iontophoresis: local experience: HKMJ, vol. 5, No. Jun. 2, 1999.

* cited by examiner

TREATMENT OF HYPERHYDROSIS

FIELD OF THE INVENTION

The present invention relates to devices and methods for the treatment of hyperhydrosis.

BACKGROUND OF THE INVENTION

Electricity may be employed to provide stimulation to the skin tissue or to facilitate drug transport across the skin barrier. In electricity-assisted devices, an electric potential (voltage) is applied to the skin membrane, to facilitate electricity passage, or ionic drug transport through the skin, the latter is called transdermal iontophoretic drug delivery. In transdermal iontophoresis, an ionized drug migrates into the skin driven by an applied electric potential gradient. Anionic drugs are delivered into the skin under the cathode (negatively charged electrode), while cationic drugs are delivered under the anode (positively charged electrode). Iontophoresis enables enhanced as well as better control of permeation rate of the ionic species into the skin.

The most common design of an iontophoresis device includes a power source (e.g., a battery), an electric control mechanism, and two separate conductive electrodes. Each conductive electrode is in contact with a separate electrolyte composition (with or without an active agent). The electrolyte or ionic active composition is generally either an aqueous solution contained in a liquid chamber or a semi-solid. The assembly of the conductive electrode and electrolyte composition is often referred to as "an electrode assembly" or simply "an electrode." The two electrode assemblies are usually affixed to the skin separated by electric insulation between them.

Alternatively, the two electrode assemblies may be constructed into a single iontophoresis device with an electric insulating material built between the two electrode assemblies for electrical isolation to prevent shorting current. An example of such an iontophoresis device is disclosed in U.S. Pat. No. 5,387,189.

In another variation of the common iontophoresis device designs, the electrolyte composition in one of the two electrode assemblies is eliminated, and the conductive electrode is placed directly in contact with the skin to complete the electric circuit. An example of such iontophoresis device is disclosed in U.S. Pat. No. 6,385,487.

During a typical iontophoresis operation (mono-polar operation), one of the two electrodes (i.e., active electrode) drives the active agent into the skin. The other electrode (i.e., disperse electrode) serves to close the electrical circuit through the skin. Sometimes, a second active agent of opposite electric charge can be placed into electrolyte composition in contact with the second electrode, thus, being delivered into the skin under the second electrode. Alternatively, the electric polarity of the first and second electrodes can be reversed periodically to drive ionic species under both electrodes (bi-polar operation). A bi-polar iontophoresis device for transdermal drug delivery is disclosed U.S. Pat. No. 4,406,658.

Iontophoretic devices are also used for the treatment of hyperhydrosis, excessive sweating typically of the palms of the hands, the soles of the feet, or the axilla. It is estimated that approximately two percent of the population suffers from hyperhydrosis. Excessive sweating can lead to further dermatological disorders and social stigma. Besides iontophoresis, conventional treatments for hyperhydrosis include the use of antiperspirants, aluminum chloride, botulinum toxin injections, and surgical procedures such as extrathoracic sympathectomy. Iontophoretic devices for the treatment of hyperhydrosis are described in example U.S. Patent Appln. Publication No. 2004/0167461 to Nitzan et al. and U.S. Pat. No. 6,223,076 to Tapper. Nitzan et al. describe the use of a dermal patch that may be in the form of an article of clothing. The patch comprises an electrochemical cell having at least two electrodes positioned on one side of the dermal patch, the electrodes forming electrical contact with a skin portion of a subject. The patch is designed and configured for delivering an electric current through the skin and conductive fluid used in conjunction with the patch.

Tapper describes the delivery of an active ingredient, such as an antiperspirant, to a region of the human body using a device comprising a DC power source, a controller and a pair of electrodes. The electrodes are mounted in generally close proximity to one another and are separated by an insulating member. The device also comprises a pair of pads, each of which is positioned in adjacent contact with one of the electrodes. The electrodes are sized and arranged so that the tissue to be treated can extend across the insulating member and simultaneously contact both pads. The entire device, for example, fits within the armpit area. See also the Drionic Device, commercially available from General Medical Company (Los Angeles, Calif.), and the MD-1a Iontophoresis Unit commercially available from R.A. Fischer Company (North Ridge, Calif.).

Conventional iontophoretic devices like the above are less than optimal. They are inconvenient to use, and immobilize the patient during treatment. They also require the use of relatively high electric currents, around 18 milliamps, that are only manually adjustable, and which may, depending on the design, be directed through major portions of the body remote from the treatment area. They are also typically painful for the person undergoing treatment due to the high current. This is a particular problem in that treatment often requires several sessions over a period of weeks or months.

Devices and methods for the treatment of hyperhydrosis have now been discovered that are simple to use, allow patient movement, and are relatively pain free. They employ a user-friendly garment, such as a glove or sock, containing a first electrode for contacting the treatment area. A second electrode is positioned on the skin nearby inside or outside the treatment area. The location of the second electrode is adjustable according to the desire and comfort of the user. A power source connects the two electrodes and provides a low, adjustable electric current to the device. Importantly, the power source provides an electric current that is customizable for the patient, for example in current intensity and treatment duration. Optionally, a carrier such as water may be used to provide ionic communication between the first electrode, the second electrode, or both, and the skin.

SUMMARY OF THE INVENTION

In one aspect, the present invention features a device for the treatment of hyperhydrosis by application of electric current to a treatment area of the skin, which comprises: a) a garment comprising a first electrode adapted for contacting said treatment area; b) a second electrode adapted for contacting said treatment area or skin proximal to said treatment area; and c) a power delivery unit in electrical communication with said first and second electrodes, wherein said power deliver unit provides a customized dose of electricity to said treatment area.

The present invention also provides a device for the treatment of hyperhydrosis by application of electric current to a palm of a human subject, which comprises: a) a glove comprising a first electrode adapted for contacting said palm; b) a second electrode adapted for location on the forearm adjacent said palm of said human subject; and c) a power delivery unit in electrical communication with said first and second electrodes, wherein said power delivery unit provides a customized dose of electricity to said palm.

The invention further provides a device for the treatment of hyperhydrosis by application of electric current to a sole of a foot of a human subject, which comprises: a) a sock comprising a first electrode adapted for contacting said sole; b) a second electrode adapted for location on the leg adjacent said foot of said human subject; and c) a power delivery unit in electrical communication with said first and second electrodes, wherein said power delivery unit provides a customized dose of electricity to said sole.

The invention also provides a method of treating hyperhydrosis by application of electric current to a treatment area of the skin, which comprises a) contacting said treatment area with a first electrode contained in a garment; b) contacting said treatment area or skin proximal to said treatment area with a second electrode, said first and second electrodes being in electrical communication with a power delivery unit; and c) providing a customized dose of electricity to said skin using said power delivery unit.

BRIEF DESCRIPTION OF THE DRAWINGS

FIG. 4b is a cross sectional view of the armband of FIG. 4a.

DETAILED DESCRIPTION OF THE INVENTION

It is believed that one skilled in the art can, based upon the description herein, utilize the present invention to its fullest extent. The following specific embodiments are merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

As used herein, "pharmaceutically-acceptable" means that the ingredients which the term describes are suitable for use in contact with the skin without undue toxicity, incompatibility, instability, irritation, allergic response, and the like.

As used herein, "safe and effective amount" means an amount of the ingredient or of the composition sufficient to provide the desired benefit at a desired level, but low enough to avoid serious side effects. The safe and effective amount of the ingredient or composition will vary with the area being treated, the age and skin type of the end user, the duration and nature of the treatment, the specific ingredient or composition employed, the particular cosmetically-acceptable carrier utilized, and like factors.

As used herein, the term "treatment" means the alleviation or elimination of symptoms, and/or cure, and/or prevention or inhibition of a disease or condition.

As used herein, "electronic communication" means the direct movement of electrons between two objects, for example the elements of the device (e.g., between the power source and the first and second electrodes).

As used herein, "ionic communication" means the movement of electrons between two objects, for example the elements of the device (e.g., the electrodes and carrier if present) and the skin, through the migration of ions as "electron movers" in contact with such objects (e.g., electrons pass between the electrodes and the skin via ionic transport of electrolytes (e.g., in the carrier) in contact with the electrode and the skin).

The device of the invention works by application of electric current to a treatment area. The treatment area may be, for example, the palm of a hand, the sole of a foot, or the axilla. In one embodiment, both electrodes are affixed to the skin but separated from one another, such that all the electric current generated by the device travels through the skin to complete the electric circuit. In one embodiment the electrodes are affixed to the skin, and physically separated, but may be in contact with the same carrier (conductive solution) such that a fraction of the current flows through the skin, and the rest flows through the carrier.

The first electrode is adapted to contact the treatment area. The second electrode may be adapted to contact skin proximal to but outside the treatment area. Alternatively, both electrodes may be in contact with the treatment area, in which case both electrodes provide treatment. Advantageously, the location of the second electrode is adjustable, to provide extra flexibility for the user. For example, the first electrode may be adapted to contact the palm of a hand and the second electrode adapted to contact any part of the adjacent forearm. Alternatively, the first electrode may be adapted to contact the sole of a foot and the second electrode adapted to contact any part of the adjacent lower leg. A variety of configurations are possible.

Garment

The first electrode (and optionally the second electrode) is held in a garment. The garment may be fabricated into various shapes and sizes to fit the contours of various anatomical surfaces of the body. For example, it may be a glove, a sock, a hat, tights, a wrap, a cuff, a band such as an armband or leg band, a shoe, a shoe insert, a belt, a vest, or a shirt. In particular, the garment may be a glove or a sock for treatment of the palm of the hand or sole of the foot, respectively. For treatment of the axilla, the garment may consist of an underarm strap.

Preferably, the garment fits the treatment area snugly to provide good contact between the first electrode and the skin of the treatment area. In one embodiment, the first electrode contacts substantially all, that is, at least 80 percent, preferably 90 percent, of the surface area of the treatment area, for example upon wetting with a carrier. More preferably, the first electrode assembly contacts all, that is, 100 percent, of the surface area of the treatment area.

Preferably, the garment is fabricated without seams to avoid nonuniform contact with the skin that may result in uneven electric current distribution.

The second electrode may be held in a separate garment. For example, in an embodiment for treatment of the palm, the first electrode may be housed in a glove, while the second in a separate armband. Alternatively, the first and second electrodes may be combined into a single garment, such as a sleeve. Additionally, the first and second electrodes may constitute separate compartments within a single garment.

The garment may be made of a variety of materials that physically stabilize the electrode(s) and the carrier. The garment should be capable of absorbing carrier. Examples of materials for use in or as the garment include, but are not limited to: cotton-based gauze; non-woven pads made of rayon or a mixture of rayon, polyester and/or other polymer fibers; felts, woven fabrics, conductive nonwoven and woven materials, open-cell foam and sponge-like materials contained of polyurethane, polyester and/or other polymers; and cross-linked and noncross-linked gelling materials, such as polyacrylamide, polyvinyl alcohol, gelatin, hydroxymethylcellulose, hydroxyethylcellulose, hydroxypropylcellulose, methylcellulose, and carboxymethyl cellulose.

In the most preferred embodiment, the material is relatively incompressible such that local variations in current density upon deformation are minimized.

Examples of further materials for use in or as the garment include, but are not limited to: hydrogels, cross-linked and non-cross-linked polymers; swellable polymers such as water-swollen cellulose derivatives (e.g., methylcellulose (MC), hydroxyethyl methylcellulose (HEMA), hydroxypropyl methylcellulose (HPMC), ethylhydroxyethyl cellulose (EHEC), hydroxyethylcellulose (HEC), hydroxypropylcellulose (HPC), and carboxymethlcellulose (CMC) and their salts); polyvinyl alcohol (PVA); polyvinylpyrrolidone (PVP); polyethylene oxide (PEO); polymers prepared by monomers such as hydroxyethyl methacrylate (HEMA), hydroxyethoxyethyl methacrylate (HEEMA), hydroxydiethoxyethl methacrylate (HDEEMA), methyoxyethyl methacrylate (MEMA), methoxyethoxyethyl methacrylate (MEEMA), methyldiethoxyethyl methacrylate (MDEEMA), ethylene glycol dimethacrylate (EGDMA), n-vinyl-2pyrrolidone (NVP), methacrylic acid (MA), and vinyl acetate (VAC); polycrylamide, polyacrylate polymers, cross-linked and non-cross-linked polyacrylic acids of various molecular weight and their salts (sodium, potassium, magnesium, calcium, aluminum, etc.); gelatin; gums and polysaccharides such as gum arabic, gum karaya, gum tragacanth, guar gum, gum benzoin, and alginic acid and their salts; polyethylene glycol (PEG); polypropylene glycol (PPG); and clays or other swellable minerals such as bentonite and montmorillonite.

In one embodiment, the material comprises a non-woven material. By "non-woven" is meant that the material, or a layer of the material, is comprised of fibers that are not woven into a fabric but rather are formed into a sheet, mat, or pad layer. The fibers can either be random (i.e., randomly aligned) or they can be carded (i.e., combed to be oriented in primarily one direction. Furthermore, the non-woven material can be composed of a combination of layers of random and carded fibers).

Non-woven materials may be comprised of a variety of natural and/or synthetic materials. By "natural" is meant that the materials are derived from plants, animals, insects, or byproducts of plants, animals, and insects. By "synthetic" is meant that the materials are obtained primarily from various man-made materials or from natural materials, which have been further altered.

Non-limiting examples of natural materials useful in the present invention are silk fibers, keratin fibers (such as wool fibers, camel hair fibers) and cellulosic fibers (such as wood pulp fibers, cotton fibers, hemp fibers, jute fibers, and flax fibers).

Examples of synthetic materials include, but are not limited to, those selected from the group containing acetate fibers, acrylic fibers, cellulose ester fibers, cotton fibers, modacrylic fibers, polyamide fibers, polyester fibers, polyolefin fibers, polyvinyl alcohol fibers, rayon fibers, polyurethane foam, and mixtures thereof.

Materials made from one or more of the natural and synthetic materials useful in the present invention can be obtained from a wide variety of commercial sources such as Freudenberg & Co. (Durham, N.C. USA), BBA Nonwovens (Nashville, Tenn. USA), PGI Nonwovens (North Charleston, S.C. USA), Buckeye Technologies/Walkisoft (Memphis, Tenn. USA), and Fort James Corporation (Deerfield, Ill. USA).

Methods of making non-woven materials are also well known in the art. Such methods include, but are not limited to, air-laying, water-laying, melt-blowing, spin-bonding, or carding processes. The resulting material, regardless of its method of production or composition, is then subjected to at least one of several types of bonding operations to anchor the individual fibers together to form a self-sustaining web. The non-woven substrate can be prepared by a variety of processes including hydro-entanglement, thermally bonding, and combinations of these processes. Moreover, the materials can have a single layer or multiple layers. In addition, a multi-layered material can include film layer(s) (e.g., aperture or non-aperture film layers) and other non-fibrous materials.

Strength, thickness, or firmness of the non-woven material may be a desirable attribute. This can be achieved, for example, by the addition of binding materials, such as wet strength resins, or the material may be made of polymer binder coatings, stable fibres, e.g. based on cotton, wool, linen and the like. Examples of wet strength resins include, but are not limited to, vinyl acetate-ethylene (VAE) and ethylene-vinyl chloride (EVCL) Airflex emulsions (Air Products, Lehigh, Pa.), Flexbond acrylic polymers (Air Products, Lehigh, Pa.), Rhoplex ST-954 acrylic binder (Rohm and Haas, Philadelphia, Pa.), and Ethylene-vinyl acetate (EVA) emulsion (DUR-O-SET® by National Starch Chemicals, Bridgewater, N.J.). The amount of binding material in the substrate may range from about 5% to about 20%, by weight, of the substrate.

Non-woven materials of increased strength can also be obtained by using the so-called spunlace or hydro-entanglement technique. In this technique, the individual fibers are twisted together so that an acceptable strength or firmness is obtained without the need to use binding materials. The advantage of the latter technique is the excellent softness of the non-woven material.

Additives may also be added in order to increase the softness of the substrates. Examples of such additives include, but are not limited to, polyols such as glycerol, propylene glycol and polyethylene glycol, phthalate derivatives, citric esters, surfactants such as polyoxyethylene (20) sorbitanesters, and acetylated monoglycerides.

Waterproofing barriers may be incorporated into the garments to prevent leakage of water from the device, which may result in loss of efficacy. They may consist of impermeable films, such as polymer or latex films, or waterproofing treatments on any of the garments surfaces.

Sensory attributes may also be incorporated to the insoluble non-woven substrates. Examples of such sensory attributes include, but are not limited to color, texture, pattern, and embossing.

It is preferred that the second electrode be placed in proximity to the first electrode (i.e. treatment site) such that electrical current passing through vital organs of the body (e.g. heart) is minimized.

For treatment of the axilla, electrode arrangement will be designed such that current through internal organs is minimized.

Power Delivery Unit

The power delivery unit delivers and controls electricity flow to the electrodes. According to the invention, it comprises a logical method to deliver a customized, predetermined dose of electricity based on user input. This provides for more comfortable and effective treatment compared with conventional devices, which typically require manual adjustment of the current intensity.

Preferably, the power delivery unit is compact, portable, convenient, and allows patient functionality and mobility during use. In one embodiment the power delivery unit may be placed on a strap around the arm with leads protruding to the first and second electrodes. Alternatively, the power delivery unit may directly attach, with electrical connectivity, to one electrode with a lead connecting to the other electrode. In other embodiments, the power delivery unit may be worn on a leg strap, belt, wristband, necklace, headband, or other similar item.

The power delivery unit may provide conventional direct current (DC) or pulsed DC, such as that disclosed in U.S. Pat. No. 5,042,975, alternating current (AC), or a combination. In one embodiment, the current density (current intensity per unit area of the skin) provided by the device in the present invention is generally less than about 0.5 mA/cm$^2$, such as less than about 0.1 mA/cm$^2$ or less than about 0.05 mA/cm$^2$. In one embodiment, the power delivery unit produces a voltage of from about 0.1 volts to about 9 volts, such as from about 1 to about 3 volts, such as about 1.5 volts. In one embodiment the power unit delivers up to but not exceeding 50 volts. The voltage may be stepped up electronically from a lower voltage. For example a 10-12 voltage may be stepped up to 50 volts.

In one embodiment, the power deliver unit is capable of automatically shutting off at the end of treatment.

The device may have built in safety features that monitor the electrical current delivered and automatically shut down the device. In one embodiment the device may have over current limit monitoring and protection with automatic shut down, with redundancy.

In one embodiment the device may include a built in electrode disconnection monitoring function with automated shut off. In one embodiment the device may include a load monitoring function to ensure that electrodes are properly attached. This function may automatically shut down the device in the case that a load is not detected.

In one embodiment, the power delivery unit is a battery (e.g., a rechargeable or disposable battery). In one embodiment, the battery is a disposable battery of small size, such as a button cell battery, suitable for a wearable patch or facial mask type adhesive device. Examples of suitable batteries include, but not limited to, button or coin batteries such as silver oxide, lithium, and zinc air batteries (which are typically used in small electronic devices). A zinc air battery is preferred because of its small size and high energy density, as well as its environmental friendliness. Examples of zinc air batteries include, but are not limited to, Energizer™ AC5 and AC10/230 (Eveready Battery Co. Inc., St. Louis, Mo.). Another preferred battery for the device is a flexible thin layer open liquid state electrochemical cell battery, such as a battery described in U.S. Pat. No. 5,897,522.

Preferably, the electric current delivered by the device to the treatment area is at a low level, for example less than about 20 milliamps or 15 milliamps, more preferably less than about 12 milliamps. Use of the device is therefore relatively pain free. In one embodiment, the electric current delivered is up to 18 milliamps. To prevent burning an other forms of skin damage, it is preferred that the current density not exceed 1 milliamp/cm2.

In one embodiment, the device further comprises means for reversing the polarity of the first and second electrodes. Such means are advantageous in that pH changes arising from electrochemical reactions involving carrier are minimized. Upon operation of the device, the polarity may automatically switch once, or multiple times, depending on current intensity and duration. In addition, the current level may be higher during periods when the anode is at the non-treatment site, such that the cycle time dedicated to offsetting pH changes is minimized, thereby reducing overall treatment time.

In another embodiment, the polarity will not require reversal at all (e.g. 18 mA). For example, at higher current intensity, treatment will be run at one polarity and then terminated. It is preferred that the treatment site be the anode during this type of treatment.

It is preferred that the first electrode be the anode at the start of operation of the device for all treatments.

In one embodiment, power delivery unit delivers a continuously increasing amount of electricity followed by a continuously decreasing amount of electricity, optionally including one or more periods of constant electricity before and/or after the periods of increasing and decreasing electricity. For example, to minimize sensation, it is preferred that electric current be gradually ramped up from zero to a maximum value and then gradually ramped down again to zero. It is preferred that changes in polarity follow a gradual ramping cycle. Ramping is controlled by the power delivery unit. In one embodiment the total ramp time may be one or two minutes, and the current may be increased and decreased in this fashion over a plurality of cycles during treatment.

As a safety feature, the length of the two leads for each electrode may be varied to reduce the chance of incorrect connection by the user. Additionally, the wire connections may only fit one port on the power delivery unit to avoid misconnection.

The power unit may be designed to include a voltage monitoring. The rationale for this is to detect sudden changes in voltage, which may be undesirable. For example, a sudden drop in voltage may indicate compromised skin permeability during treatment (e.g. cut, blister formation). Sudden increased voltages may indicate loss of contact or less contact area and subsequent higher current density.

In an alternate embodiment, the device may be comprised of a galvanic couple of materials which generates electricity through electrochemical reactions initiated upon wetting of the system as disclosed in the US Patent Application Publication Nos. 2004/0267237, 2005/0004509, and 2005/0148996. For example zinc ink or another anodic ink may be screen-printed as the first electrode while silver-silver chloride ink or another cathodic ink may be printed as the second electrode. Electrodes may be in a one or two compartment arrangement and are activated upon wetting with carrier. Galvanic couples may also be created by conductive laminate materials.

Alternatively, the device may comprise electrodes in particulate form, for example particles comprising the first electrode and particles comprising the second electrode, or single particles comprising both the first electrode and second electrode, i.e., particles of the first electrode coated with second electrode material. Electrical current may be delivered to the skin using galvanic microparticles as described in the US Patent Application Publication No. 2007/0060862 A1.

Customized Dose

Figure 1:
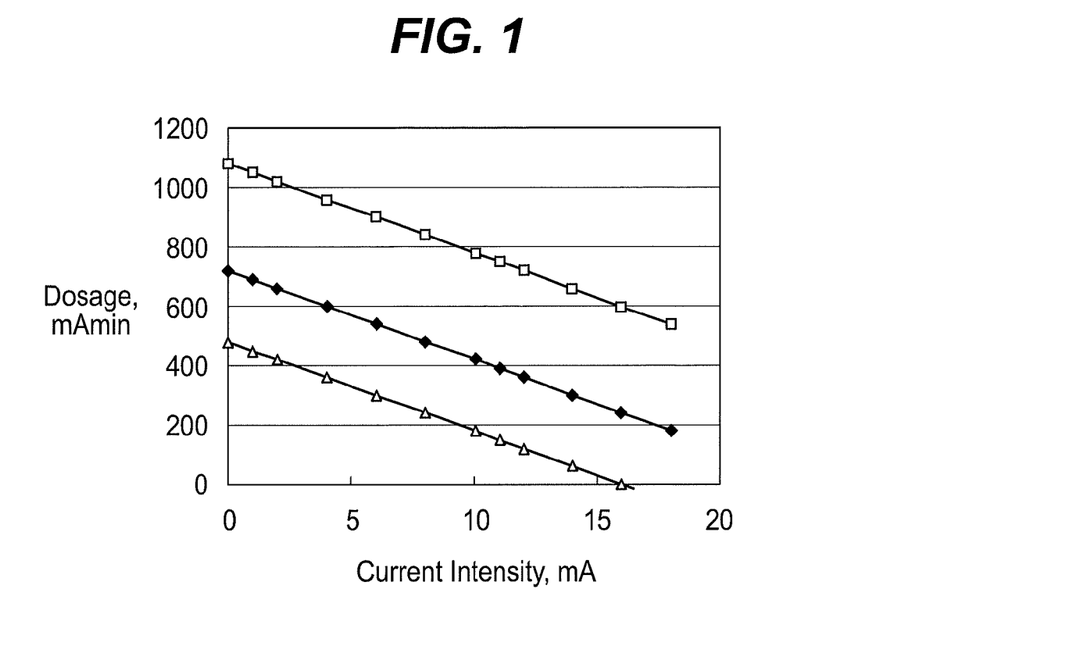
FIG. 1 is a graph demonstrating the range of electricity dosage as a function of current intensity. The top and bottom curves illustrate maximum and minimum values, respectively. The intermediate line represents most preferred dosage value.
Figure 2:
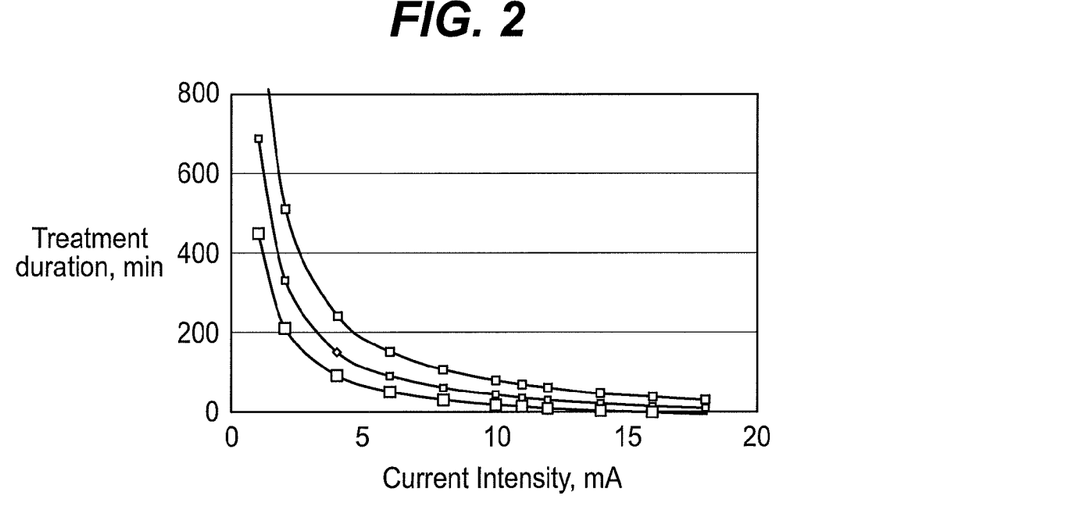
FIG. 2 is a graph showing the treatment duration corresponding to the dosage curves of FIG. 1.

According to the invention, the electrical dose (mA min) delivered by the device may be customized and determined by an algorithm that uses the current intensity (mA) to calculate the appropriate dose for the user. Current intensity is selected by the user based on his tolerance level for the treatment and severity of condition. Based on this, the power delivery unit delivers a customized dose (z) to the user employing, for example, the following algorithm:

$$z=360(1+x)$$

such that the benchmark dosage (360 mA min) is multiplied by a factor of 1+x to account for changes in current intensity (i). x varies with current intensity as:

$$x=(A-i/2)/6$$

where A is a factor defined as follows. The claimed dose range is that which is comprised of the space between the dosage curves arising from the above equations with A=2.0 and A=24. FIG. 1 shows the respective curves (triangles A=2, squares A=24). The most preferred dosage value is that obtained from a value of A=12 (diamonds). FIG. 2 depicts a graph showing the treatment duration corresponding to the dosage curves of FIG. 1.

Carrier

In one embodiment, the first electrode, the second electrode, or both are in ionic communication with a carrier containing an electrolyte. In the preferred embodiment, the first electrode and carrier for first electrode are separate from the second electrode and carrier for second electrode. The same or different carriers may be used with each electrode. The carrier may be a liquid (e.g., a solution, a suspension, or an emulsion that may be immobilized within the garment comprising an absorbent material such as gauze, cotton or non-woven pad made of synthetic or natural cellulose materials), a semi-solid (e.g., a gel, a cream, a lotion, microemulsion, or hydrogel), or a solid (e.g., a lyophilized foam composition that may be reconstituted by adding a liquid prior to use to form a gel) that during use is capable of conducting electricity from an electrode (e.g., the carrier may contains one or more electrolytes and water).

In one embodiment, the carrier (e.g., a liquid or semi-solid) is added to the first electrode by the user prior to or after applying the first electrode to the treatment area. For example, the carrier is added to a material for use in or as the garment (discussed below) comprising the first electrode. In one embodiment, the material is an absorbent material that can immobilize the carrier (such as gauze or non-woven pad) that contains or is in contact with the electrode (e.g., the first electrode is contained within or affixed to the absorbent material).

In one embodiment, the carrier is manufactured and placed in storage as a stable nonconductive composition (e.g., an anhydrous composition with negligible conductive ions). Prior to or during the use, as an activation step, water is mixed into the anhydrous composition to significantly increase its conductivity by enabling the passage of an electric current through the system. Examples of the carrier include, but are not limited to, purified water, tap water, distilled water, deionized water, skin creams, lotions, and polar solutions. Other examples of carriers include biological fluids or excretion such as sweat, skin moisture, interstitial fluid, intercellular fluid, wound exudates, blood, saliva, menstrual fluid, tears, urine, and vaginal fluid that exit the body and enter into the reservoir of the device. Examples of electrolytes include, but are not limited to, pharmaceutically acceptable organic and inorganic acids, bases, salts, buffers, peptides, polypeptides, proteins, nucleic acids, and/or other inorganic and organic compounds. Examples of inorganic salts include, but are not limited to, chloride salts (such as sodium chloride, potassium chloride, lithium chloride, calcium chloride, strontium chloride, magnesium chloride or other chloride salts), as well as salts of sodium, potassium, lithium, calcium, magnesium, strontium, fluoride, iodide, bromide. Examples of buffers include, but are not limited to, phosphates, citrates, acetates, lactates, and borates.

In one embodiment, the electrolyte is an active agent, or becomes an active agent after the passage of the electric current through the carrier. Examples of such electrolyte-active agents include, but are not limited to (anticholinergics) and other weak acid or weak base active agents.

In one embodiment, the carrier contains water. In a further embodiment, the carrier may also contain one or more organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols.

In one embodiment, the carriers of the first and second electrode may be different. For example, the carrier for the first electrode may be purified water and the carrier for the second electrode may be a buffered solution.

Examples of glycols include, but are not limited to, glycerin, propylene glycol, butylene glycol, pentalene glycol, hexylene glycol, polyethylene glycol, polypropylene glycol, diethylene glycol, triethylene glycol, glycerol, and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol.

The organic solvents may be present in the carrier in an amount, based upon the total weight of the carrier, of from about 1 percent to about 90 percent (e.g., from about 5 percent to about 50 percent). Water may be present in the carrier (prior to use) in an amount, based upon the total weight of the carrier, of from about 5 percent to about 95 percent (e.g., from about 50 percent to about 90 percent).

In one embodiment, the carrier is a nonconductive carrier such as an anhydrous composition that contains organic solvents that interact strongly when mixed with water during the application, resulting in the release of solvation heat to increase the temperature of the carrier and/or the power delivery unit, consequently increasing the electric current generated by either the battery or the galvanic power source. Examples of such organic solvents include, but are not limited to, glycerol, glycols (e.g., propylene glycol, butylenes glycol and ethylene glycol) and polyglycols (e.g., polyethylene glycols of various molecular weight, such as PEG400 and polypropylene glycols of various molecular weights).

The carrier may also contain: preservatives (such as cresol, chlorocresol, benzyl alcohol, methyl p-hydroxylbenzoate, propyl p-hydroxybenzoate, phenol, thimerosal, benzalkonium chloride, benzethonium chloride, and phenylmercuric nitrate); stabilizing agents or antioxidants (such as ascorbic acid, ascorbic acid esters, butylhydroxy anisole, butylhydroxy toluene, cysteine, N-acetylcysteine, sodium bisulfite, sodium metabisulfite, sodium formaldehydesulfoxylate, acetone sodium bisulfite, tocopherols, and nordihydroguaiaretic acid); chelating agents (such as ethylenediaminetetraacetic acid and its salts); buffers (such as acetic acid, citric acid, phosphoric acid, glutamic acid, and salts thereof); and tonicity adjusting agents (such as sodium chloride, sodium sulfate, dextrose and glycerin).

In one embodiment, the carrier is present in at least about 50%, such as at least about 75%, by weight, of the total weight of the garment prior to use. In another embodiment, (i) liquid carrier is present in less than about 10%, such as less than about 1%, by weight of the total weight of the garment (for example, the garment may not contain any carrier prior to use). In a further embodiment, the device is accompanied by instructions for the user to either (i) wet the garment prior to application or (ii) wet the skin with water and/or another liquid prior to or after application.

Electrodes

The electrodes may be reactive conductive electrodes or inert conductive electrodes. As used herein, a "reactive conductive electrode" is an electrode that undergoes a change in chemical composition during the chemical reactions occurring due to passage of electric current through the electrode. In one embodiment, the reactive conductive electrode is made of reactive materials such as metal halides (e.g., silver-silver chloride (Ag/AgCl), silver-silver bromide, and silver-silver iodide). In this case, the primary electrochemical reaction at the cathode surface is conversion of solid silver halide to metallic silver with little unwanted consumption of the oxidizing agents generated by the anode. The released halide ions may be subsequently oxidized to oxidizing agents, such as chloride ions to chlorine ($Cl_2$), hypochlorous acid (HClO), and hypochlorite ions ($ClO^-$), and iodide ions to iodine.

As used herein, an "inert conductive electrode" is an electrode that does not undergo a change in its chemical composition. In one embodiment, an inert conductive electrode is made of, or coated on the surface with, an inert materials such as noble metals (e.g., gold, platinum, gold-coated conductive metals), conductive carbon (e.g., glassy carbon or graphite), carbon-embedded polymers (e.g., conductive carbon silicone rubbers or conductive vinyl polymers), conductive carbon polymer foam or sponge, silver halide-coated silver (e.g., silver chloride-coated silver, silver bromide-coated silver, and silver iodide-coated silver), and corrosive resistant alloys such as stainless steel. Flexible and conformable conductive polyvinyl sheet electrode, manufactured by a printing or laminating method, is a preferred electrode material in the present invention.

Electrodes may also include conductive or metal plates, foils, meshs, or foams, or conductive non-woven or woven material embedded with thin metal wire such as stainless wire.

Electrodes may also be comprised of conductive woven or nonwoven materials. In one embodiment, the electrode may be a nonconductive woven or nonwoven specially knit with conductive fibers In addition, electrodes may be composed of printed or sprayed conductive inks. Inks can be composed of conductive particles, such as carbon, silver, or stainless steel. The ink may contain a solvent and polymeric binder. Such printed or sprayed conductive films can be sprayed onto garment (i.e. nonwoven, socks), or other electrode supporting substrates (e.g. nitrile glove).

Electrodes may be molded to fit three dimensional surfaces of the body such as the underarm, or soles of the feet. This may be achieved either by molding conductive materials such as conductive polymers or metals, or by molding a nonconductive surface and laminating or spraying a conductive medium onto its surface to realize the three dimensional shape. For example, a nonconductive sole insert may be sprayed or screen printed with conductive ink, or laminated with conductive laminate to provide the conductive surface on the insole.

It is preferred that the surface area of the second electrode exceed that of the first electrode to reduce current density at the nontreatment surface, thereby reducing user sensation. Preferably, the surface area of the second electrode is more than two fold that of the first electrode. Alternately, in the case of lower intensity treatments where sensation may be minimal, it is desired that the second electrode be smaller than in high intensity treatment (less surface area). Also, it may be preferable that the second be equal to or smaller than the first electrode.

Electrode connections between the power delivery unit and electrodes may be completed using solder, conductive adhesive, lamination, electrical snaps, or other electrical connections. It is preferred that such connections be easy to attach for the everyday user. It is preferred that any conductive exposed wiring or connection junction to the electrodes be isolated from the carrier in order to avoid ion release into the carrier and eliminating undesired ionic delivery to the user, which may cause irritation. Electrical junctions may be isolated by coating with nonconductive or conductive polymer, covering with nonconductive or conductive laminate, adhesive, or tape.

In another embodiment, the electrical power may be transmitted wirelessly through RF technology, such that no electrical connectivity is needed between the power unit and electrodes.

In the most preferred embodiment, the electrodes may be arranged in such a way that all the current of the first electrode travels into the skin and returns through the second electrode (two compartment system). In another embodiment, a fraction of the current of the first electrode travels through the skin while the remaining fraction travels only through the carrier and/or solution (one compartment system) as disclosed in the US Patent Application Publication No. 2004/0267169.

Figure 3A:
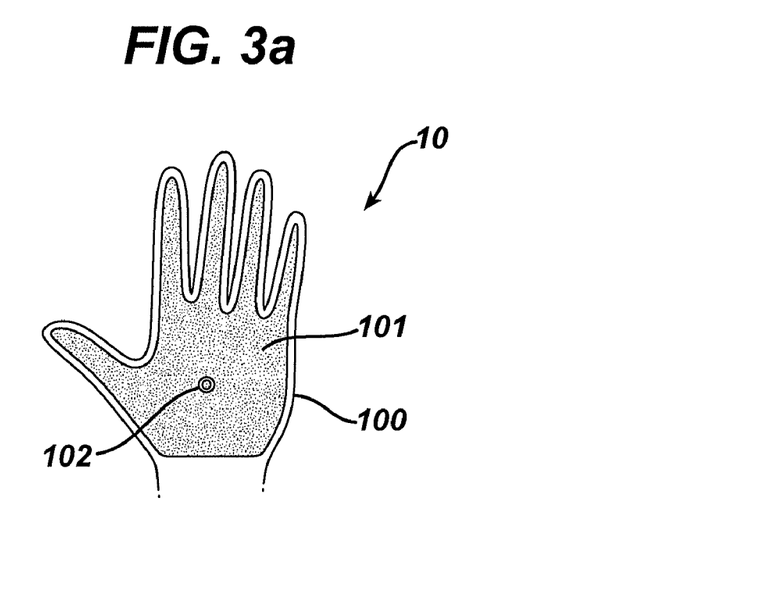
FIG. 3a an inside-out view of a glove housing an electrode according to the invention.

Referring to the drawings, FIG. 3a shows an inside-out view of a garment 10 consisting of an outer glove 100 housing an electrode 101 on the palmar side. A conductive metallic snap 102 provides electrical connectivity between the electrode 101 and the outside of the glove.

Figure 3B:
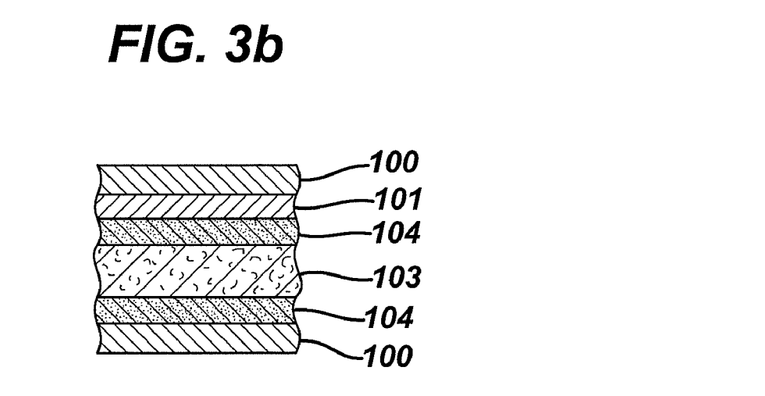
FIG. 3b is a cross sectional view of the layers of the glove of FIG. 3.

FIG. 3b shows a cross sectional view of the garment of FIG. 3a in use. Hand 103 is in contact with wet absorbent material 104. Electrode 101 is present on the palmar side of the hand only.

Figure 4A:
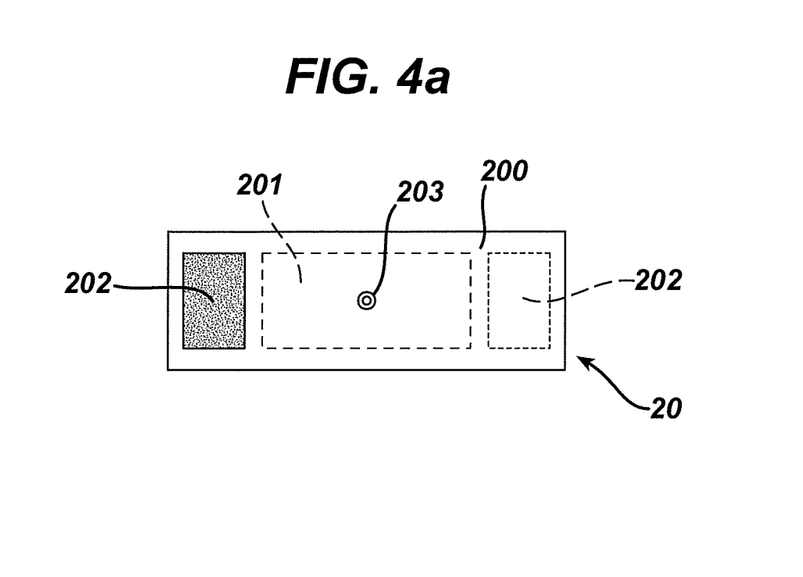
FIG. 4a depicts an armband housing an electrode according to the invention.

FIG. 4a shows a top view of a multilayered armband garment 20 composed of an outer layer of absorbent material 200 enclosing an electrode 201. The ends of the garment are fitted with velcro 202 such that the user can affix the armband firmly to the arm. An electrical snap 203 provides electrical connectivity between the electrode 201 and the outside surface of the garment.

Figure 4B:
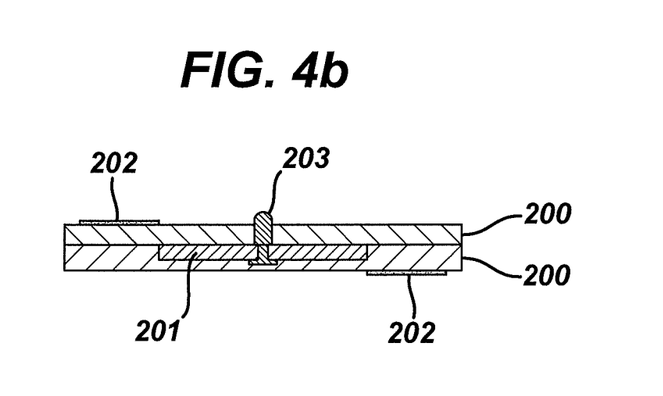

FIG. 4b is a cross sectional view illustrating the layers of the garment in FIG. 4a.

Figure 5:
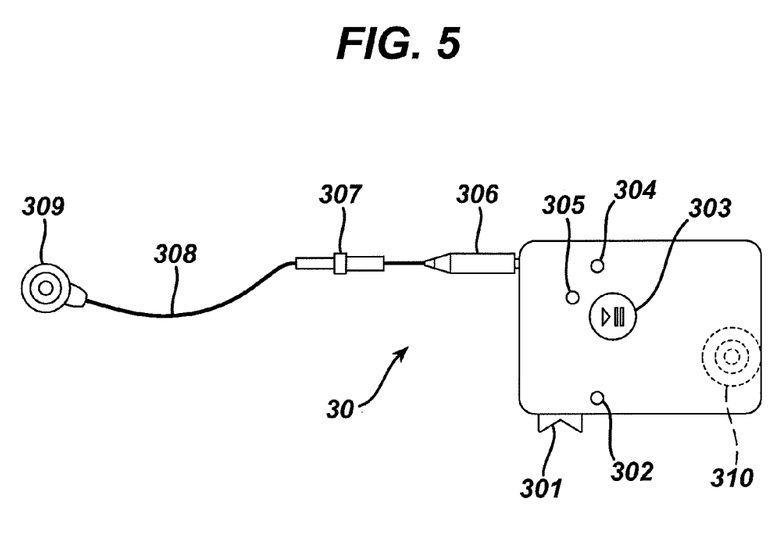
FIG. 5 depicts a power delivery unit according to the invention.

FIG. 5 shows a power delivery unit 30 according to the invention. The power on/off switch 301 is toggled to activate or deactivate the device. An LED 302 indicates when the system is on. The treatment start/stop/pause button 303 is also shown. Two additional LED's represent diagnostic indicator 304 and "in-process" indicator 305. The output plug 306 is connected to an inline fuse 307 and leads, via the positive electrode lead 308, to a positive lead snap connector 309. A negative lead port 310 is located on the bottom of the power delivery unit.

Figure 6:
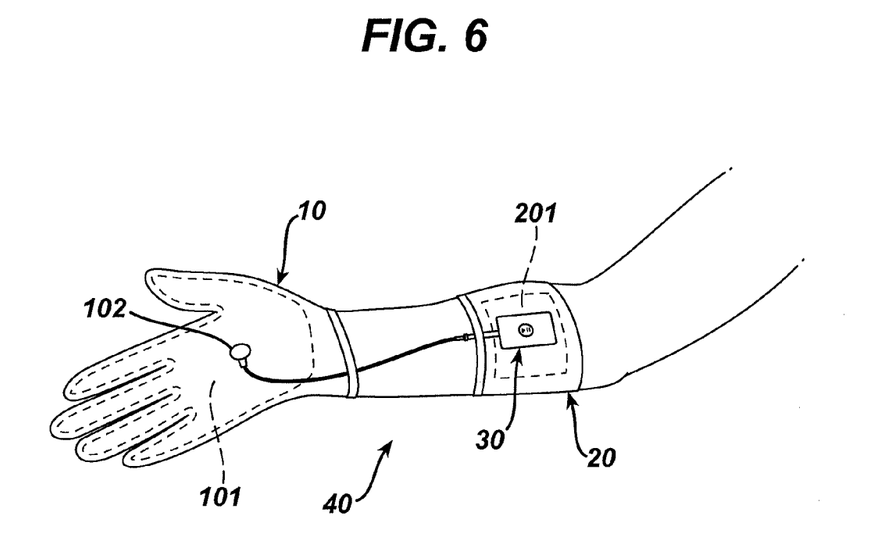
FIG. 6 depicts a device according to the invention on a person's arm during treatment.

FIG. 6 demonstrates a device 40 according to the invention as worn during treatment. Electrode 101, which is in the shape of a palm and lies beneath the glove 10, is shown as a dashed line. Similarly, electrode 201 contained in armband garment 20, is shown as a dashed line. The negative snap 310 of the power delivery unit 30 is connected to the armband snap 203.

Active Agents

In one embodiment, the device also delivers one or more active agents into the skin. Such active agents include those either initially incorporated in the carrier or electrochemically generated by the electric current passing from an electrode through a carrier during use. Examples of useful active agents for the treatment of hyperhydrosis include antiperspirants, in particular aluminum-containing antiperspirants such as aluminum chlorohydrate or aluminum-zirconium.

In one embodiment, the carrier contains metals such as metal ions or fine powders. Examples of such metals include, but are not limited to, gold, silver, copper, zinc.

The amount of the active agent in the carrier will depend on the active agent and/or the intended treatment area. In one embodiment, the carrier contains a safe and effective amount of the active agent, for example, from about 0.001 percent to about 20 percent, by weight, such as from about 0.01 percent to about 5 percent, by weight, of the carrier.

Use

The device is used for the treatment of hyperhydrosis. Although applicants do not wish to be bound by theory, it is believed that the application of electric current to the skin using the device plugs the pores of the treatment area, thereby preventing sweating. Alternatively, it may have a possible effect on the sweat gland by disturbing the electrical gradient that is thought to cause the movement of sweat along the sweat duct. The device is used by placing the garment over the treatment area (optionally using a carrier such as water), such that the first electrode is in contact with the treatment area. Ideally, the garment will have a shape and size approximating the treatment area, as described herein, and first electrode will contact substantially all, preferably all of the treatment area. The second electrode is placed on the skin at a location within the treatment area or proximal to but outside of the treatment area. The current intensity is determined, and then the power delivery unit is activated and set at the desired current intensity, whereupon the power delivery device determines the correct treatment duration, after which the device preferably automatically turns off. Optionally, the polarity of the first and second electrodes are periodically reversed, such that electric current flows in one direction, then the opposite direction. Ideally, this device can be fully administered and operated by the user with no assistance needed from others.

In one treatment regimen the user may select from several current intensities based on his comfort requirements. The device automatically calculates the appropriate treatment duration of treatment corresponding to the user's desired treatment intensity and delivers the appropriate amount of electricity. The device may allow users the ability to choose from a continuous set of current intensities within a restricted range. Alternatively, the device may offer one or more predetermined treatment intensities (e.g. low, medium, or high).

Total electrical dose (e.g. charge, mA min) delivered to the skin may be prescribed by a physician and precisely monitored by the power delivery unit throughout treatment. In one embodiment, the physician may prescribe the total electrical dose (mA min), while the user chooses the desired current intensity of treatment (mA). In this embodiment the power delivery unit will monitor the length of treatment to achieve the desired dosage. Treatment duration is often longer than three minutes, preferably from 20-480 minutes. In another embodiment, the total dose and treatment duration are determined by the logarithm mentioned above.

In the case that a user or clinician wishes to pause treatment and continue shortly thereafter, the power delivery unit may include a treatment pause feature which ramps current to zero within a predetermined time interval. Treatment may resume, taking into account the paused time, as indicated by user or clinician. Current will ramp back to the treatment current and continue as programmed.

In one regimen, it may be desired that the user rub a thin layer of insulating material, such as silicone gel or petroleum jelly, over the skin prior to treatment. The rationale for this is that it has been shown that a thin layer of silicone gel enhances the efficacy of iontophoresis treatment for hyperhydrosis (Sato, K., Timm, D. E., Sato, F., Templeton, E. A., Meletiou, D. S., Toyomoto, T., Soos, G., Sato, S. K. Generation and Transit Pathway of H+ Ion is Critical for Inhibition of Palmar Sweating by Iontophoresis in Water. *Journal of Applied Physiology*. 75(5) 1993).

Combination with Other Energy Forms

It may be desirable to combine use of the present device with other therapeutic forms of energy. For instance, in one embodiment the carrier may be heated to and maintained at, for example, about 35-45° C. This will result in sweat pore dilation during treatment and enhance treatment efficacy of the present invention. Additionally, warming may reduce unpleasant sensation of electric current. Heating may be achieved by building an ohmic, radio frequency, or infrared heating unit into the garments as well known in the art. The heating may also be generated from redox reactions unit such as disclosed in the U.S. Pat. No. 6,890,553 or from hydration heating when water is added to the system as disclosed in the U.S. Pat. No. 7,005,408. In another embodiment, it is desirable to cool the garment to alleviate sensation. This may be achieved by an electronic cooling unit, or by adding cooling salts to the solution. In yet another embodiment, it is desirable to couple electric treatment of present invention with ultrasound or laser treatment. In another embodiment, it is desirable to use a combination of the above-mentioned energies together.

EXAMPLES

The following examples illustrate use of the device to provide customized doses of electricity according to the invention using the algorithm described above. In each case, the user sets the current intensity, and the power delivery unit calculates the dose.

Case 1: User A selects current intensity of 12 mA (constant)—According to the algorithm, at 12 mA, the device delivers a predetermined dosage within the range of 120-720 mA min, with the preferred value at 360 mA min. Assuming a dosage level of 360 mA min, the power delivery unit delivers 12 mA for 30 minutes.

Case 2: User B selects a current intensity of 8 mA (constant)—According to the algorithm, at 8 mA, the device delivers a predetermined dosage within the range of 240-840 mA min, with the preferred value at 480 mA min. Assuming a dosage level of 480 mA min, the power delivery unit delivers 8 mA for 60 minutes.

Case 3: User C selects 10 mA (constant) for an early phase of treatment, then increases to 16 mA (constant) several weeks later. The user decides to change levels because his tolerance of the current increased—According to the algorithm, at the 10 mA initially chosen by the user, the dosage range is between 180-780 mA min, with the preferred value at 420 mA min. Assuming a dosage level of 420 mA min, the treatment duration is 42 minutes.

Several weeks later, when the user switches to a 16 mA current level, the dosage level changes to a range of 0-600 mA min, with the most preferred value of 240 mA min. Assuming 240 mA min, the treatment duration is 15 minutes.

Case 4: User D sets the current intensity to 6 mA and runs the treatment for 10 minutes, then increases the current intensity to 10 mA for the remainder of treatment because he can tolerate the treatment—Initially the current intensity is set to 6 mA. At this current intensity, the algorithm calls for a dosage range of 300-900 mA min, with the preferred dosage being 540 mA min. If 6 mA is delivered to the patient for 10 minutes, then 60 mA min of electrical dose is administered in that time.

If the user changes the current intensity to 10 mA, then a new dosage must be calculated for the remainder of treatment. At 10 mA, the algorithm calls for 180-780 mA min with the preferred value at 420 mA min. 60 maA min is delivered to the user during the first phase of treatment. The total remaining dosage (at 10 mA) is 360 mA min. To deliver 360 mA min at a 10 mA current level, the remaining duration of treatment is 36 minutes. Thus, the user undergoes 46 minutes of total treatment.

We claim:

1. A device for the treatment of hyperhydrosis by application of electric current to a treatment area of the skin, which comprises:
   a) a garment comprising a first electrode adapted for contacting said treatment area;
   b) a second electrode adapted for contacting the treatment area or skin proximal to the treatment area; and
   c) a power delivery unit in electrical communication with said first and second electrodes, wherein said power deliver unit provides a customized dose of electricity to said treatment area, wherein said customized dose of electricity comprises one or more cycles of a gradually increasing amount of electricity, followed by a first period of constant electricity, followed by a gradually decreasing amount of electricity, followed by a second period of constant electricity.

2. The device of claim 1, wherein said power delivery unit is capable of automatically shutting off at the end of treatment.

3. The device of claim 1 further comprising one or more carriers in ionic communication with said first electrode, said second electrode, or both, wherein said carriers are in contact with the skin.

4. The device of claim 1, wherein said garment is selected from the group consisting of gloves, socks, hats, tights, wraps, cuffs, armbands, leg bands, shoes, shoe inserts, belts, underarm straps, vests, and shirts.

5. The device of claim 1, wherein said power delivery unit provides an electric current of less than about 18 milliamps.

6. The device of claim 1, wherein said garment comprises a material comprising a non-woven.

7. The device of claim 1, wherein said power delivery unit is a direct current power delivery unit.

8. The device of claim 1 further comprising means for reversing the polarity of said first and second electrodes.

9. The device of claim 1, wherein said customized dose is calculated using the algorithm:

$$z=360(1+x)$$

wherein z is said customized dose, x is defined as:

$$x=(A-i/2)/6$$

i is current intensity, and A is 2 to 24.

10. A device for the treatment of hyperhydrosis by application of electric current to a palm of a human subject, which comprises:
    a) a glove comprising a first electrode adapted for contacting said palm;
    b) a second electrode adapted for location on the forearm adjacent said palm of said human subject; and
    c) a power delivery unit in electrical communication with said first and second electrodes, wherein said power deliver unit provides a customized dose of electricity to said palm, wherein said customized dose of electricity comprises one or more cycles of a gradually increasing amount of electricity, followed by a first period of constant electricity, followed by a gradually decreasing amount of electricity, followed by a second period of constant electricity.

11. The device of claim 10, wherein said power delivery unit is capable of automatically shutting off at the end of treatment.

12. The device of claim 10 further comprising one or more carriers in ionic communication with said first electrode, said second electrode, or both, wherein said carriers are in contact with the skin.

13. The device of claim 10, wherein said garment comprises a material comprising a non-woven.

14. The device of claim 10, wherein said customized dose is calculated using the algorithm:

$$z=360(1+x)$$

wherein z is said customized dose, x is defined as:

$$x=(A-i/2)/6$$

i is current intensity, and A is 2 to 24.

15. A device for the treatment of hyperhydrosis by application of electric current to a sole of a foot of a human subject, which comprises:
    a) a sock or shoe comprising a first electrode adapted for contacting said sole;
    b) a second electrode adapted for location on the leg adjacent said foot of said human subject; and
    c) a power delivery unit in electrical communication with said first and second electrodes, wherein said power deliver unit provides a customized dose of electricity to said sole, wherein said customized dose of electricity comprises one or more cycles of a gradually increasing amount of electricity, followed by a first period of constant electricity, followed by a gradually decreasing amount of electricity, followed by a second period of constant electricity.

16. The device of claim 15, wherein said power delivery unit is capable of automatically shutting off at the end of treatment.

17. The device of claim 14 further comprising one or more carriers in ionic communication with said first electrode, said second electrode, or both, wherein said carriers are in contact with the skin.

18. The device of claim 14, wherein said garment comprises a material comprising a non-woven.

19. The device of claim 15, wherein said customized dose is calculated using the algorithm:

$$z=360(1+x)$$

wherein z is said customized dose, x is defined as:

$$x=(A-i/2)/6$$

i is current intensity, and A is 2 to 24.

20. A method of treating hyperhydrosis by application of electric current to a treatment area of the skin, which comprises
   a) contacting said treatment area a first electrode contained in a garment;
   b) contacting the treatment area or skin proximal to the treatment area with a second electrode, said first and second electrodes being in electrical communication with a power delivery unit; and
   c) providing a customized dose of electricity to said skin using said power delivery unit, wherein said customized dose of electricity comprises one or more cycles of a gradually increasing amount of electricity, followed by a first period of constant electricity, followed by a gradually decreasing amount of electricity, followed by a second period of constant electricity.

21. The method of claim 20, wherein at least one of said first electrode and said second electrode are in ionic communication with one or more carriers and said carriers are in contact with said skin, whereby said electric current is also conducted through said carriers.

22. The method of claim 20, wherein said garment is selected from the group consisting of gloves, socks, hats, tights, wraps, cuffs, armbands, leg bands, shoes, shoe inserts, belts, underarm straps, vests, and shirts.

23. The method of claim 20, wherein said garment is a glove.

24. The method of claim 20, wherein said power delivery unit provides an electric current of less than about 18 milliamps.

25. The method of claim 20, wherein said electric current is a direct current.

26. The method of claim 20 further comprising periodically reversing the polarity of said first and second electrodes.

27. The method of claim 20, wherein said customized dose is calculated using the algorithm:

$$z=360\,(1+x)$$

wherein z is said customized dose, x is defined as:

$$x=(A-i/2)/6$$

i is current intensity, and A is 2 to 24.

* * * * *